United States Patent [19]

Klein et al.

[11] 4,163,783

[45] * Aug. 7, 1979

[54] SYNERGISTIC COMPOSITIONS AND METHOD OF USE TO TREAT INFLAMMATION

[76] Inventors: Robert W. Klein, 1013 Union Meeting Rd., Blue Bell, Pa. 19422; George W. Nuss, Jr., 1505 Taylor Rd., Lansdale, Pa. 19446

[ * ] Notice: The portion of the term of this patent subsequent to May 1, 1996, has been disclaimed.

[21] Appl. No.: 901,573

[22] Filed: May 1, 1978

Related U.S. Application Data

[63] Continuation-in-part of Ser. No. 835,595, Sep. 22, 1977.

[51] Int. Cl.$^2$ .................... A61K 31/44; A61K 31/555

[52] U.S. Cl. .................... 424/245; 424/263; 424/274; 424/317; 424/DIG. 4

[58] Field of Search .................... 424/263, DIG. 4, 245

[56] References Cited

U.S. PATENT DOCUMENTS

| | | | |
|---|---|---|---|
| 3,346,578 | 10/1967 | Langlykke et al. | 424/263 |
| 3,890,434 | 6/1975 | Weisse et al. | 424/DIG. 4 |
| 3,928,605 | 12/1975 | Curry | 424/DIG. 4 |
| 4,049,665 | 9/1977 | Douglas | 424/DIG. 4 |

*Primary Examiner*—Stanley J. Freidman

[57] ABSTRACT

The present invention relates to a novel synergistic composition and to a method of treating inflammation in warm blooded animals by topically administering to a warm blooded animal in need of such treatment an effective amount of the synergistic combination of a non-steroidal agent having anti-inflammatory activity and bis-(2-pyridyl-1-oxide) disulfide and/or at least one adduct of bis-(2-pyridyl-1-oxide) disulfide having the empirical formula:

$$(C_5H_4NOS)_2MY_t \qquad (I)$$

wherein M represents a member selected from the group consisting of zinc, iron, magnesium, tin, cadmium, zirconium, alkali and alkaline earth metals; Y is the anion of an inorganic acid and t is either 1 or 2.

2 Claims, No Drawings

SYNERGISTIC COMPOSITIONS AND METHOD OF USE TO TREAT INFLAMMATION

BACKGROUND OF THE INVENTION

This application is a continuation-in-part of application Ser. No. 835,595, filed Sept. 22, 1977.

The present invention relates to the novel method of treating inflammation in mammals by administering the synergistic combination of a non-steroidal agent having anti-inflammatory activity and bis-(2-pyridyl-1-oxide) disulfide and/or at least one metal salt of bis-(2-pyridyl-1-oxide) disulfide and to novel compositions containing such compounds.

Bis-(2-pyridyl-1-oxide) disulfide (also referred to as 2,2'-dithiodipyridine-1-1'-dioxide) and various derivatives thereof, have previously been disclosed in the literature. For example, U.S. Pat. No. 2,742,476 discloses bis-(2-pyridyl-1-oxide) disulfide and the lower alkyl substituted derivatives thereof. U.S. Pat. No. 3,027,371 discloses molybdate derivatives, U.S. Pat. No. 3,027,732 discloses stannous chloride derivatives and U.S. Pat. 3,346,578 discloses stannous fluoride derivatives of bis-(2-pyridyl-1-oxide) disulfide and each refer to the anti-fungal and antibacterial properties of said derivatives.

U.S. Pat. No. 3,890,434 discloses hair and antiseptic formulations containing adducts of bis-(2-pyridyl-1-oxide) disulfide with alkaline earth metal salts.

Co-pending application Ser. No. 835,596, of R. W. Klein et al relates to a composition and method for treatment of inflammation through the use of the synergistic combination of a corticosteroid and the metal salts of bis-(2-pyridyl-1-oxide) disulfide.

U.S. Pat. No. 3,600,437 discloses the preparation of α-methyl-3-phenoxybenzeneacetic acid.

U.S. Pat. Nos. 3,228,831 and 3,385,886 disclose the preparation of 4-(2-methylpropyl) benzeneacetic acid and α-methyl-4-(2-methylpropyl)benzeneacetic acid.

U.S. Pat. No. 3,637,776 discloses the preparation of α,2-(6-methoxy-2-naphthyl) propionic acid.

U.S. Pat. No. 3,161,654 discloses the preparation of 1-(p-chlorobenzoyl)-5-methoxy-α-methylindole-3-acetic acid.

U.S. Pat. No. 3,714,226 discloses the preparation of 2',4'-difluoro-4-hydroxy-3-biphenylcarboxylic acid.

DETAILED DESCRIPTION OF THE INVENTION

Now it has been found that even more pronounced pharmacological properties for the relief and inhibition of inflammation conditions can be provided by the topical administration of the combination of a non-steroidal agent having anti-inflamatory properties and bis-(2-pyridyl-1-oxide) disulfide and/or its adducts according to this invention. More specifically, these adducts have the formula:

$$(C_5H_4NOS)_2MY_t \qquad (I)$$

wherein M represents a member selected from the group consisting of zinc, iron, magnesium, tin, cadmium, zirconium, alkali and alkaline earth metals; Y is the anion of an inorganic or organic acid and t is either 1 or 2. More particularly, the anion Y is selected from the group consisting of halides, sulfates, nitrates, chlorates and acetates, with the chlorides and sulfates being most preferable. More particularly preferred are the water soluble adducts, especially calcium chloride ($CaCl_2$) or magnesium sulfate ($MgSO_4$). Also included in the adducts of this invention are the hydrates of the aforementioned compounds, i.e., adducts including $nH_2O$ groups where n is an integer of 0 to 10. Additionally, the adducts (I) may contain one or more substituents on either or both pyridine ring structures such as alkyls, halogens and alkoxy groups. It is further noted that $(C_5H_4NOS)_2$ as used in (I) above and throughout the specification and claims represents bis-(2-pyridyl-1-oxide) disulfide and the structural formula shown as follows:

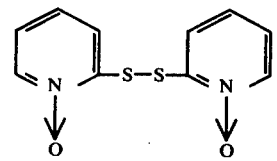

Among the active ingredients which may be utilized in combination with the non-steroidal agents having anti-inflammatory activity in this invention may be mentioned: Bis-(2-pyridyl-1-oxide) disulfide, bis-(2-pyridyl-1-oxide) disulfide magnesium sulfate, bis-(2-pyridyl-1-oxide) disulfide magnesium acetate, bis-(2-pyridyl-1-oxide) disulfide magnesium chloride, bis-(2-pyridyl-1-oxide) disulfide magnesium bromide, bis-(2-pyridyl-1-oxide) disulfide calcium chloride, bis-(2-pyridyl-1-oxide) disulfide calcium sulfate, bis-(2-pyridyl-1-oxide) disulfide calcium nitrate, bis-(2-pyridyl-1-oxide) disulfide calcium acetate, bis-(2-pyridyl-1-oxide) disulfide calcium chlorate, bis-(2-pyridyl-1-oxide) disulfide barium chloride, bis-(2-pyridyl-1-oxide) disulfide barium sulfate, bis-(2-pyridyl-1-oxide) disulfide barium nitrate, bis-(2-pyridyl-1-oxide) disulfide barium acetate, bis-(2-pyridyl-1-oxide) disulfide barium chlorate, bis-(2-pyridyl-1-oxide) disulfide strontium chloride, bis-(2-pyridyl-1-oxide) disulfide strontium sulfate, bis-(2-pyridyl-1-oxide)disulfide strontium nitrate, bis-(2-pyridyl-1-oxide) disulfide strontium acetate, bis-(2-pyridyl-1-oxide) disulfide strontium chlorate, bis-(2-pyridyl-1-oxide) disulfide potassium chloride, bis-(2-pyridyl-1-oxide) disulfide potassium sulfate, bis-(2-pyridyl-1-oxide) disulfide potassium nitrate, bis-(2-pyridyl-1-oxide) disulfide potassium acetate, bis-(2-pyridyl-1-oxide) disulfide potassium chlorate, bis-(2-pyridyl-1-oxide) disulfide sodium chloride, bis-(2-pyridyl-1-oxide) disulfide sodium sulfate, bis-(2-pyridyl-1-oxide) disulfide sodium nitrate, bis-(2-pyridyl-1-oxide) disulfide sodium acetate, bis-(2-pyridyl-1-oxide) disulfide sodium chlorate, bis-(2-pyridyl-1-oxide) disulfide zinc chloride, bis-(2-pyridyl-1-oxide) disulfide zinc sulfate, bis-(2-pyridyl-1-oxide) disulfide zinc nitrate, bis-(2-pyridyl-1-oxide) disulfide zinc acetate, bis-(2-pyridyl-1-oxide) disulfide zinc chlorate, bis-(2-pyridyl-1-oxide) disulfide stannous chloride, bis-(2-pyridyl-1-oxide) disulfide stannous sulfate, bis-(2-pyridyl-1-oxide) disulfide stannous nitrate, bis-(2-pyridyl-1-oxide) disulfide stannous acetate, bis-(2-pyridyl-1-oxide) disulfide stannous chlorate, bis-(2-pyridyl-1-oxide) disulfide zirconium chloride, bis-(2-pyridyl-1-oxide) disulfide zirconium sulfate, bis-(2-pyridyl-1-oxide) disulfide zirconium nitrate, bis-(2-pyridyl-1-oxide) disulfide zirconium acetate, bis-(2-pyridyl-1-oxide) disulfide zirconium chlorate, bis-(2-pyridyl-1-oxide) disulfide ferrous chloride, bis-(2-pyridyl-1-oxide) disulfide ferrous sulfate, bis-(2-pyridyl-1-oxide) disulfide ferrous nitrate.

bis-(2-pyridyl-1-oxide) disulfide ferrous acetate, bis-(2-pyridyl-1-oxide) disulfide ferrous chlorate, bis-(2-pyridyl-1-oxide) disulfide lithium chloride, bis-(2-pyridyl-1-oxide) disulfide lithium sulfate, bis-(2-pyridyl-1-oxide) disulfide lithium nitrate, bis-(2-pyridyl-1-oxide) disulfide lithium acetate, and bis-(2-pyridyl-1-oxide) disulfide lithium chlorate.

A number of known effective anti-inflammatory non-steroidal agents may be utilized in this invention. Among the suitable non-steroidal agents may be mentioned 1-(p-chlorobenzoyl)-5-methoxy-2-methylindole-3-acetic acid d-2-(6-methoxy-2-naphthyl) propionic acid, 1-methyl-5-(4-methylbenzoyl-1 H-pyrrole-2-acetic acid, α-methyl-4-(2-methylpropyl) benzeneacetic acid, 4-(2-methylpropyl)benzeneacetic acid, α-methyl-3-phenoxybenzeneacetic acid, α, 3-dichloro-4-cyclohexylphenylacetic acid, 2'4'-difluoro-4-hydroxy-3-biphenylcarboxylic acid, and the like.

It has been surprisingly found that the anti-inflammatory activity of bis-(2-pyridyl-1-oxide) disulfide and/or its adducts I is enhanced when combined with other known effective non-steroidal anti-inflammatory agents.

In accordance with the present invention, a method of treating inflammation in warm blooded animals is provided which comprises topically administering to a warm blooded animal in need of such treatment an effective amount of the combination of at least one of the aforementioned non-steroidal agents and bis-(2-pyridyl-1-oxide) disulfide and/or the adducts of Formula I.

As used herein, the term "treatment" is meant to include both active treatment and preventative or prophylactic treatment.

The present invention also has for its object compositions and means for treating warm-blooded animals requiring anti-inflammatory treatment for skin conditions such as contact dermatitis, seborrheic dermatitis, atopic dermatitis, neurodermatitis and the like as well as a wide variety of mammalian conditions where the symptoms of inflammation and associated fever and pain manifest, such as in rheumatic diseases including arthritis, tendinitis, sciatic pain, erythema, and similar associated veterinary conditions, a composition containing the combination of a non-steroidal agent having anti-inflammatory activity and at least bis-(2-pyridyl-1-oxide) disulfide or one of its adducts I in an amount of from about 0.05-10% by weight of the composition, preferably from about 0.25-5.0% by weight. The non-steroidal agents are utilized in the composition in an amount of 1-40% by weight of bis-(2-pyridyl-1-oxide) disulfide compound in the composition, preferably 5-25% by weight of the compound present. These compositions can be in the form of a solution, a cream, powder, gel, ointment, salve, lotion, or milk. For the treatment of skin conditions, they can also constitute make-up products or dermatological cakes containing the ingredients standard to this type of composition.

Various tests in animals can be carried out to show the ability of the active compounds of this invention to exhibit reactions that can be correlated with anti-inflammatory activity in humans. One such test is the Carrageenan paw edema test, which shows the ability of the instant compounds to inhibit edema induced by injection of an inflammatory agent such as carrageenan into the tissues of the paw of a rat against non-inflamed controls. This carrageenan testing method is known to correlate well with anti-inflammatory activity in humans and is a standard test used to determine anti-inflammatory activity. This correlation can be shown by the activities of compounds known to be clinically active including such as aspirin, phenylbutazone, cortisone, hydrocortisone and prednisolone. In view of the results of this test, the active compounds and derivatives can be considered to be active anti-inflammatory agents. Other tests which can be correlated to show significant activities are the "polyarthritis in rats" and "ultra-violet erythema in guinea pigs".

The following Examples will further illustrate the formulations containing the non-steroidal agents and bis-(2-pyridyl-1-oxide) disulfide or adducts I but are not to be considered as limiting the scope of this invention.

EXAMPLE 1

| A cream was prepared as follows: | |
|---|---|
| Bis-(2-pyridyl-1-oxide) disulfide calcium chloride | 1 g |
| 1-(p-chlorobenzoyl)-5-methoxy-2-methylindole-3-acetic acid | 0.3 g |
| Titanium oxide | 10 g |
| Red iron oxide | 0.3 g |
| Yellow iron oxide | 0.2 g |
| Brown iron oxide | 0.4 g |
| Chestnut iron oxide | 0.2 g |
| Stearyl alcohols oxyethylenated with 33 mols of ethylene oxide | 7 g |
| Polyglycol stearate | 6 g |
| Propyl parahydroxybenzoate | 0.2 g |
| Water, Q.S.P. | 100 g |

Other creams identical to that described immediately above are prepared by replacing the calcium chloride compound with any of the previously mentioned active compounds.

EXAMPLE 2

A dermatological cleansing cake is prepared by mixing together the following components:

| | |
|---|---|
| Esters of sodium isothionate and coprafatty acids (sold under the tradename "IGEPON A" having the formula R—COO—CH$_2$—CH$_2$—SO$_3$Na, wherein R equals fatty acid derivatives having 12-15 carbon atoms) | 75 g |
| Lanolin derivatives | 22.75 g |
| (C$_5$H$_4$NOS)$_2$ . MgCl$_2$ | 1 g |
| d-2-(6-methoxy-2-naphthyl) propionic acid | 1 g |

Other dermatological cleansing cakes, identical to the above, are prepared by replacing the magnesium chloride salt of bis-(2-pyridyl-1-oxide) disulfide with any one of the aforementioned active compounds. Also, any one of the non-steroidal agent mentioned may be utilized.

EXAMPLE 3

A powder comprising the following mixture:

| | |
|---|---|
| Talc | 86.85 g |
| Glycerine oleate | 3 g |
| Isopropyl myristate | 7 g |
| Bis-(2-pyridyl-1-oxide) disulfide magnesium sulfate | 1 g |
| 1-methyl-5-(4-methylbenzoyl-1 H-pyrrole-2-acetic acid | 1 g |

| | |
|---|---|
| -continued | |
| Perfume | 2cc(= approx. 1.9g) |

Other equally effective powder compositions identical to the above are prepared except that the active ingredient component bis-(2-pyridyl-1-oxide) disulfide magnesium sulfate is replaced by any of the other aforementioned active compounds.

EXAMPLE 4

Cocoa butter (approximately 40 g) is mixed with bis-(2-pyridyl-1-oxide) disulfide zinc acetate approximately 1 g and α-methyl-4-(2-methylpropyl)benzeneacetic acid (0.1) and the resulting mixture is melted with gentle heat and poured into a mold of suitable size and shape.

EXAMPLE 5

The following ointment base was utilized as a vehicle for the active ingredients of this invention:

| Ingredient | Amount in grams |
|---|---|
| Polyoxyethylene stearyl ether | 5.0 |
| White petrolatum | 5.0 |
| Stearyl alcohol | 15.0 |
| Distilled water | 63.5 |

The ointment containing the above active ingredients was manufactured in the following manner. 1.00 gram bis-(2-pyridyl-1-oxide) disulfide magnesium sulfate were dissolved in a heated mixture of 61.5 ml. of distilled water and 11.50 g of propylene glycol. This solution was heated to a temperature of 75° C. and added to a mixture having a like temperature consisting of 0.5 g of 4-(2-methylpropyl) benzeneacetic acid, 15.0 g of stearyl alcohol, 5.0 g of white petrolatum, 1.0 ml of concentrated ammonium solution and 5.0 g of polyoxyethylene stearyl ether, molecular weight about 700. While the resulting mixture was still hot, lactic acid was added to adjust the pH thereof to about 5.5 to approximate the pH of skin. The resulting mixture was thereafter cooled to form a cream which was further worked utilizing a three-roller frame and filled into tubes.

In an analogous manner, ointments with 4-(2-methylpropyl) benzeneacetic acid were prepared utilizing the following ingredients to form the initial solutions:

a. 4.27 grams bis-(2-pyridyl-1-oxide) disulfide ferrous chloride in 53.23 ml of distilled water and 11.5 g of propylene glycol;

b. 4.51 grams of bis-(2-pyridyl-1-oxide) disulfide lithium acetate in 56.19 ml of distilled water and 11.5 g of propylene glycol;

c. 4.62 grams of bis-(2-pyridyl-1-oxide) disulfide zirconium chloride in 56.35 ml of distilled water and 11.5 g of propylene glycol;

d. 2.0 grams of bis-(2-pyridyl-1-oxide) disulfide strontium chloride in 60.7 ml of distilled water and 11.5 g of propylene glycol.

In this example the solution was heated to 75° C. and added to a mixture having a like temperature and containing 4.5 grams of bis-(2-pyridyl-1-oxide) disulfide magnesium sulfate, 0.45 α-methyl-3-phenoxybenzeneacetic acid, 13.0 grams of stearyl alcohol, 5.0 grams of polyoxyethylene stearyl ether, molecular weight about 700 and 5.0 grams of white petrolatum, the pH was adjusted with lactic acid and the mixture cooled to form a cream which was worked up as above.

EXAMPLE 6

An ointment was prepared by first mixing 2.0 g of bis-(2-pyridyl-1-oxide) disulfide magnesium sulfate, 2.0 g of bis-(2-pyridyl-1-oxide) disulfide magnesium chloride and 1.0 g of α-3,-dichloro-4-cyclohexylphenylacetic acid in a hot mixture of 57.5 g of distilled water and 11.5 g of propylene glycol.

EXAMPLE 7

An aerosol preparation was formed from the following formulation:

| Phase I | |
|---|---|
| Ingredient | Weight in grams |
| Isopropyl myristate | 18 |
| Stearate acid, cosmetic grade | 30 |
| Myristic acid, cosmetic grade | 9 |
| Glycerin | 18 |
| Phase II | |
| Ingredient | Weight in grams |
| Water | 440 |
| Triethanolamine | 20 |
| Bis-(2-pyridyl-1-oxide) disulfide calcium chloride | 22 |
| Phase III | |
| Ingredient | Weight in grams |
| Panthenol | 6 |
| Suitable perfume | 3 |
| 2,4'-difluoro-4-hydroxy-3-biphenylcarboxylic acid | 12 |
| Lactic acid q.s.pH | 5.5 |

Phase I and Phase II were separately heated at a temperature of about 75° C. Thereafter, Phase II was added dropwise with vigorous stirring to Phase I which was maintained at a temperature of 75° C. The mixture was then cooled to above 50° C. with stirring and the first three ingredients of Phase III added thereto. The resulting emulsion was mixed and the pH adjusted to about 5.5 with lactic acid. The emulsion was then cooled with stirring to about 20° C.

Nine parts by weight of the emulsion formed above were combined with one part by weight of a propellant (40 dichlorodifluoromethane/60 dichlorotetrafluoroethane) under pressure in suitable aerosol container equipped with conventional valve apparatus and foam-forming head.

EXAMPLE 8

An anti-inflammatory composition in milk form having the following composition:

| Ingredient | Weight in grams |
|---|---|
| Hydrogenated, ethoxylated (10 mol) lanolin | 1.8 |
| Triglyceride of fatty acid of coconut | 7.0 |
| Cetylalcohol | 0.6 |
| Stearylalcohol | 0.6 |
| Paraffin oil (lightweight) | 5.0 |
| α,3-dichloro-4-cyclohexyl-phenylacetic acid | 0.75 |
| Stearic acid | 3.0 |
| Bis-(2-pyridyl-1-oxide) disulfide magnesium sulfate | 2.0 |
| Demineralized water | 72.2 |
| Triethanolamine | 0.8 |
| Perfume | 0.5 |
| Carboxyvinylpolymer 941 | 1.0 |

| Ingredient | Weight in grams |
| --- | --- |
| Conservation agent | 2.0 | was manufactured as follows:

A mixture of 1.8 g hydrogenated, ethoxylated (10 mol) lanolin, 7.0 g triglyceride of fatty acid of coconut, 0.6 g cetylalcohol, 0.6 g stearyl alcohol, 5.0 g paraffin oil, 0.75 g α,3-dichloro-4-cyclohexylphenylacetic acid and 3.0 g of stearic was blended at 70° C. After addition of 4.0 g bis-(2-pyridyl-1-oxide) disulfide magnesium sulfate, 2.0 g carboxyvinylpolymer in 72.2 g demineralized water were added at 70° C. with stirring to the resulting suspension. The mixture was stirred for 15 minutes and then cooled to 50° C. The 0.8 g of triethanolamine and 0.5 g of perfume were added at 50° C. and 45° C. respectively. The resulting mixture was stirred until cold and a white mile was obtained. Viscosity: 4,000 Cp (Brookfield, Spindel, 5 at 10 Rpm).

What is claimed is:

1. A method of treating inflammation in warm blooded animals which comprises topically administering to a warm blooded animal in need of such treatment an effective amount of a non-steroidal agent having anti-inflammatory activity selected from the group consisting of 1-(p-chlorobenzoyl)-5-methoxy-2-methylindole-3-acetic acid, d-2-(6-methoxy-2-naphthyl)propionic acid, 1-methyl-5-(4-methylbenzoyl-1)H-pyrrole-2-acetic acid, α-methyl-4-(2-methylpropyl)benzeneacetic acid, 4-(2-methylpropyl)benzeneacetic acid, α-methyl-3-phenoxybenzeneacetic acid, α,3-dichloro-4-cyclohexylphenylacetic acid, 2',4'-difluoro-4-hydroxy-3-biphenylcarboxylic acid and bis-2-(pyridyl-1-oxide) disulfide, said non-steroidal agent being present in the amount of 1–40% by weight of said bis-(2-pyridyl-1-oxide) disulfide.

2. A composition for topically treating inflammation in warm blooded animals which comprises about 0.05 to about 5% by weight of the total composition of the combination of a non-steroidal agent having anti-inflammatory activity selected from the group consisting of 1-(p-chlorobenzoyl-5-methoxy-2-methylindole-3-acetic acid, d-2-(6-methoxy-2-naphthyl)propionic acid, 1-methyl-5-(4-methylbenzoyl-1)H-pyrrole-2-acetic acid, α-methyl-4-(2-methylpropyl)benzeneacetic acid, 4-(2-methylpropyl)benzeneacetic acid, α-methyl-3-phenoxybenzeneacetic acid, α,3-dichloro-4-cyclohexylphenylacetic acid, 2',4'-difluoro-4-hydroxy-3-biphenylcarboxylic acid and bis-(2-pyridyl-1-oxide)disulfide together with a suitable pharmaceutical carrier, said non-steroidal agent being present in the amount of 1–40% by weight of said bis-(2-pyridyl-1-oxide) disulfide.

* * * * *